United States Patent [19]
Morita et al.

[11] Patent Number: 6,031,157
[45] Date of Patent: Feb. 29, 2000

[54] **VARIETY OF *STEVIA REBAUDIANA* BERTONI**

[75] Inventors: Toyoshige Morita; Yucheng Bu, both of Osaka, Japan

[73] Assignee: Morita Kagaku Kogyo Co., Ltd., Osaka, Japan

[21] Appl. No.: 09/013,029

[22] Filed: Jan. 26, 1998

[30] Foreign Application Priority Data

Jan. 30, 1997 [JP] Japan ................................. 9-016531
Jan. 23, 1998 [JP] Japan ................................. 10-011205

[51] Int. Cl.[7] ................................. A01H 5/10; A01H 5/00; A01H 1/04
[52] U.S. Cl. ................................. 800/298; 800/260; 800/263
[58] Field of Search ................................. Plt./100; 800/298, 800/260, 263

[56] References Cited

U.S. PATENT DOCUMENTS

P.P. 10,564  8/1998  Marsolais et al. ................. Plt./100
4,590,160  5/1986  Nishihashi et al. ................. 435/78

OTHER PUBLICATIONS

Brandle et al. Heritability for yield, leaf:stem ratio and stevioside content estimated from a landrace cultivar of *Stevia rebaudiana*. Canandian Journal of Plant Science. 72:1263–1266, 1992.

Shyu et al. Effects of harvesting dates on the characteristics, yield, and sweet components of stevia (*Stevia rebaudiana* Bertoni) lines. Journal of Agricultural Researc of China. 43:29–39, 1994.

Hsu et al. Effects of harvesting dates on the characters, yield, and sugar components of different *Stevia rebaudiana* lines. Journal of Agricultural Research in China, vol. 43, No. 1, pp. 29–38. Translation pp. 1–27, 1994.

*Primary Examiner*—Lynette R. F. Smith
*Assistant Examiner*—Melissa L. Kimball

[57] ABSTRACT

The present invention provides seeds for cultivation of a new variety of *Stevia Rebaudiana* Bertoni, the new variety, a sweetening obtained from dried leaves of the new variety and a process for production of the sweetening.

4 Claims, No Drawings

VARIETY OF STEVIA REBAUDIANA BERTONI

BACKGROUND OF THE INVENTION

1. Field of the Invention

The present invention relates to a seed for cultivation of a new variety of *Stevia rebaudiana* Bertoni capable of growing leaves containing Rebaudioside A at a high proportion, a new variety of *Stevia rebaudiana* Bertoni capable of being cultivated by seed propagation and also a sweetening produced therefrom and a process for producing the sweetening.

2. Description of the Prior Art

Stevia is a perennial plant of compositae, of which the provenance is Paraguay and the scientific name is *Stevia rebaudiana* Bertoni. Stevia contains sweetening components of about 300 times the sweetness of sugar and therefore is cultivated for use in sweetening ingredients as a natural sweetening.

As the sweetening components of Stevia, Stevioside ($C_{38}H_{60}O_{18}$, molecular weight of 804), Rebaudioside A ($C_{44}H_{70}O_{23}$, molecular weight of 966), Rebaudioside C, D, E and Dulcoside A, etc are known.

In the varieties of Stevia generally cultivated, a major component of the sweetening components is Stevioside (ST), the content of Rebaudioside A is about 3 to 4 tenths and that of Rebaudioside C is a little less. However the components of Stevia depend on the variety, for-example, one variety does not contain Rebaudioside A or C, and in another variety, the major component is Rebaudioside C.

Sweetness is a particularly delicate sense among the senses which are perceived by the tongue, for example, when compared with astringent or pungent taste. The degree of the sweetness of Stevioside is about 300 times as sweet as sugar and therefore is used as a sweetening in the food industry. The sweetness of Stevioside is relatively similar to that of sugar, but has a disadvantage in that it leaves some unpleasant tastes such as a bitter taste. In other words, it is undesirable for a sweetening to contain large amounts of Stevioside. On the contrary, Rebaudioside A has a good quality sweetness and the degree of sweetness is 1.3 to 1.5 times as sweet as Stevioside.

The inventors of the present invention carried out plant breeding by the repetition of crossing selection to obtain varieties of Stevia which show a high content ratio of Rebaudioside A (RA) in relation to Stevioside (ST). They have produced an excellent sweetening by extracting sweetening components from a variety of Stevia (Japanese Patent Publication A Nos. 59-045848 (1984) and 61-202667 (1986)).

However, the content proportion of Rebaudioside A in the above mentioned varieties decreases in plants cultivated by seed propagation, for example, a plant from a seed in a ratio of ST:RA of 1:4 grows leaves in a ratio of ST:RA of 1:1 to 1.5. Therefore, in order to keep a high content proportion of Rebaudioside A, cuttage has been used.

In addition, *Stevia rebaudiana* Bertoni is self-incompatibile and therefore, the harvested seeds do not always germ. That is, the germination percentage is low. That is the reason why Stevia has been cultivated by cuttage and those skilled in the art would not consider cultivating Stevia by seed propagation.

However, since the number of cuttings obtained from a parent plant are limited and many parent plants are needed, it is difficult to cultivate a large quantity of rooted cuttings.

The inventors intensively studied Stevia capable of being cultivated by seed propagation while maintaining a high content of Rebaudioside A.

SUMMARY OF THE INVENTION

The inventors of the present invention established by d selection a new variety of *Stevia rebaudiana* Bertoni which has a gene expressing a high content of Rebaudioside A and can dominantly transmit the gene to the next generation by seed propagation.

Therefore, it is an object of the present invention to provide a seed for cultivation of a variety of *Stevia rebaudiana* Bertoni capable of growing leaves containing 2.56 times or more Rebaudioside A than Stevioside. The leaves of a plant produced from the seeds for cultivation are used for the production of a sweetening.

It is an object of the invention to provide a new variety of *Stevia rebaudiana* Bertoni capable of being cultivated by seed propagation.

It is an object of the invention to provide a sweetening containing 2.56 times or more Rebaudioside A than Stevioside by a process for production which comprises extracting dried leaves of *Stevia rebaudiana Bertoni* containing 2.56 times or more Rebaudioside A than Stevioside with water or an aqueous solvent and isolating sweetening components from the resulting extract.

It is an object of the invention to provide a process for production of a sweetening containing 2.56 times or more Rebaudioside A than Stevioside obtained by a process for production which comprises extracting dried leaves of *Stevia rebaudiana* Bertoni containing 2.56 times or more Rebaudioside A than Stevioside with water or an aqueous solvent and isolating sweetening components from the resulting extract.

DETAILED DESCRIPTION OF THE INVENTION

The variety of *Stevia rebaudiana* Bertoni of the present invention was produced by the protocol shown in Table 1 below.

The parent plants are owned by the inventors and guaranteed to be transferred according to the Japanese Patent rule 27 ter.

TABLE 1

SF3
    selfing
    harvesting seeds
    seeding

SF3 grade selection
(less than 1: more than 2.54)(= SF3 grade)
    selfing
    harvesting seeds
    seeding
    selection SF4
(SF3 grade)

TABLE 1-continued

```
        |
       selfing
       harvesting seeds
       seeding
       selection
        |
       SF5
(less than 1: more than 3)
        |
       selfing
       harvesting seeds
       seeding
        |
       SF6
   (average 1: 3)
```
The ratio given in parentheses
shows Stevioside:Rebaudioside A Production of the new variety of the invention Hills (SF3 grade) containing 2.56 times or more Rebaudioside A than Stevioside were selected from seeds formed by crossing between SF3s described in Japanese patent Publication A No. 61-202667. This disclosure is incorporated herein by reference.

Further, crossing and selection were repeated and as a result of crossing between both hills containing 2.56 times or more Rebaudioside A than Stevioside, SF5-1 (designated No. 103), which is excellent in a disease resistance to Septoria, and SF5-2 (designated No. 109), which is excellent in sweetening components, were finally selected.

The seeds from the crossing between No. 103 and No. 109 were sowed and cultivated. More than 80% of the resulting hills contained 2.56 times or more Rebaudioside A than Stevioside and the hills are almost established (SF6-1). However, crossing between SF3 and No. 103 or No. 109 was carried out, seeds were formed on No. 103, No. 109 and SF3, but cultivation using the seeds formed on SF3 did not give hills containing a stable component proportion of Rebaudioside A.

Cultivation Method of Stevia

A sowing bed is prepared, into the lower part of which fine soil or sand are put so that it is well drained and a small amount of fertilizer is preferably added. After making layers with fine particles, about 10 mesh, of soil or Vermiculite in size SS (Commercial name, Asahi Kogyo Co. Ltd.) and the like, the upper part of the sowing bed is well moistened by sprinkling water. The temperature of the sowing bed is kept at 20 to 25° C. until seeding. The seeds may keep any papi, but these are, however, preferably removed in order to allow good contact with the soil.

After being soaked in water for one day, the seeds are mixed with fine soil of about 10 mesh or Vermiculite in SS size and the like to be well dispersed and sowed. After being settled by sprinkling enough water, the seeds are covered by cheese cloth to shut out direct rays of sunlight. The surface of the ground is kept wet and then the seeds germ. The number of days for germination is 7–14 days; however, in case of slow germination or a low temperature, it will take longer.

The temperature and water are carefully controlled in the period until the germination of Stevia is completed. After germination, Stevia is gradually exposed to sunlight and if necessary, liquid fertilizer is applied.

In case of temporary planting, when nursery stocks grow 2 to 3 cm, they are transplanted. When breeding pots or breeding trays are used as sowing beds, transplantation is unnecessary.

At the time when the nursery stocks have developed about 10 cm, they are transplanted to a field. The field is previously fertilized and ridged sufficiently for the number of planting stocks. The number of planting stocks is preferably 100,000–150,000 per hectare, but if desired the number may be changed. The amount of fertilizer depends on the grade of soil fertility, generally, nitrogenous, phosphate and potash fertilizers may each be used in amounts of about 200 kg per 1 hectare. After transplantation, the field is well watered in order to maintain close contact with seeds and to lessen the damage of transplantation. In a region in a low latitude, the plants may bloom in a early stage of the growing period. When buds or flowers appear, they should be picked. In the growing period, weeding and water control and also, if necessary, additional fertilization is carried out. In times of high temperature and in high humidity, a bactericide is sprinkled.

After the plants grow to more than about 30 cm in height, and when buds and flowers appear, the plants are harvested leaving the lower two or three pairs of leaves. After the harvest, leaf parts are removed from the plants to apply to solar drying or hot wind drying, or plant types as such may be applied to solar drying or hot wind drying. The leaf parts are classified into leaves, stems and branches and the leaves are used for a raw material of a sweetening as dry leaves.

Preparation of Sweetening Sample

Twenty grams of dry leaves are extracted with 10 to 20 parts of water several times. The resulting extracts are combined and passed slowly through a column filled with 20 ml of cation-exchange resin (Amberlite IR-120B) and then a column filled with 20 ml of anion-exchange resin (Dulite AD-4). Then the treated solution is passed through a column packed with 100 ml of a resin for absorption (Amberlite XAD-2) to absorb the sweetening components, and then washed fully with water. After this water is drained from the column, which is eluted with 30 ml of methanol to isolate the sweetening components. The eluent is concentrated and further dried under a reduced pressure to obtain a pale yellow powder.

Method of Analysis

1) High Performance Liquid Chromatography

A sweetening sample is dissolved into the following eluent to subject to a column.

Column package: lichrosorb $NH_2$ $5\mu$

Flow rate: 1.5 ml/min

Eluent: acetonitrile:water=80:20

Measured wave length: 210 nm

2) Thin-layer Chromatography

A sweetening sample is dissolved into water to put on a thin-layer plate.

Instrument: Shimazu chromato scanner type 910

Thin-layer plate: silica gel 60F254 (Merc)

Developing solution: chloroform:Methanol:water= 30:20:4

Developer: 50% sulfuric acid

Method for measurement: reflective zigzag scanning method

Scan speed: 20 nm/min

The sweetening of the present invention can be produced as described above and the yield is about 12 to about 13% by weight based on dried leaves. Conventional cation-exchange resin and anion-exchange resin may be used in the present invention. The aqueous solvent may be that of methanol or ethanol.

The sweetening of the present invention may be used as such and also as a sweetening composition, which may include conventional food additives such as diluents, for example, dextrin, starch or glucose. An appropriate amount of the sweetening of the invention may be added to foods, drinks, medicines and the like.

EXAMPLE

Example 1
Production of SF4 and Analysis

At the end of February 1994, a sowing bed with an electric heater wires was prepared in a greenhouse made of vinylon in the Niimi factory of Morita Kagaku Kogyo Co. Ltd. At the lower part of the sowing bed, 2 g of fine soil, sand and chemical fertilizers (nitrogenous, phosphate and potash, each 8% by weight) were added per 1 liter of soil and the mixture was laid to a depth of 5 cm, and at the upper part, soil which was previously sieved through a 10 mesh sieve and Vermiculite in size SS were mixed in a ratio of 1:1. After the mixture was laid to a depth of 3 cm, the sowing bed was sufficiently sprinkled to dampen it and the temperature was kept at 20 to 25° C. After the pappi of seeds harvested from SF3 in 1993 were removed, the seeds were soaked for one day and mixed with Vermiculite in size SS and the mixture was seeded. After seeding, the seeds were well settled by sprinkling enough water and then covered by a cheese cloth to shut out direct rays of sunlight. The humidity and temperature of the sowing bed were maintained. After 14 days from seeding, the sowing bed was gradually exposed to the sun, and At 3 weeks after seeding, 50 time-diluted liquid fertilizer was applied to it.

When seedlings of Stevia became 2 to 3 cm in height, the same soil as in the sowing bed was put into a cultivating box, 1500 seedlings were temporarily planted at intervals of 4 cm in the cultivating box and the temperature was maintained by a vinylon tunnel.

In the beginning of May, when the seedlings had grown to about 10 cm in height, the seedlings were transplanted to a field at intervals of 25×30 cm. The field was previously ridged up to 60 cm in width of raw space and 250 kg of a chemical fertilizer was applied per 10 ares of the field.

After transplantation, the field was well watered. Weeding and water control were well accomplished in the growth period and in June, an additional 40 kg per 10 ares of fertilizer was applied to the field. In the rainy season, 1000 time-diluted solution of sterilizers Hansen and Captan (Commercial names) were sprinkled two times a week.

After the 20th day of July, 900 of hills of good growth were selected and the plants were harvested leaving the lower 5 pairs of leaves, and the leaves were separated from the plants for solar drying. The dried leaves were treated as described above to prepare a sweetening sample, which was analyzed by thin-layer chromatography.

According to the thin-layer chromatography, 21% of the hills were found to have a ratio of Stevioside:Rebaudioside of less than 1:more than 2.54, and 5.7% of the hills were in a ratio of Stevioside:Rebaudioside of less than 1:more than 3. The average ratio of Stevioside:Rebaudioside was found to be less than 1:more than 1.43.

Five hills of the same grade of growth as SF3, cuttings of which had planted in the middle of April and transplanted to the field in the beginning of May and, of the same ratio of sweetening components as SF3 were selected and designated SF4.

Example 2
Production of SF5-1 and SF5-2 and Analysis

At the end of July 1494, 20 hills each derived from 5 hills of SF4 mentioned above were multiplicated by cuttage and were grown in a vinylon greenhouse and the SF4 were self-crossed. From the beginning of November, 2000 seeds were obtained from SF4.

In 1995, 1500 seeds of SF4 were sowed and cultivated as described above. After the 20th day of July, 650 of hills of good growth were selected from the obtained 1200 seedlings and the plants were harvested leaving the lower 5 pairs of leaves and the leaves were separated from the plants for solar drying. The dried leaves were analyzed by thin-layer chromatography.

According to the thin-layer chromatography, the hills having a ratio of the sweetening components Stevioside Rebaudioside of less than 1:more than 2.54 only were selected. The percentage of such hills were found to be 39%; and 6.5% of the hills had a ratio of Stevioside:Rebaudioside of less than 1 : more than 3. The average ratio of Stevioside:Rebaudioside was found to be 1:1.21. Among the hills in a ratio of Stevioside:Rebaudioside of less than 1:more than 3, 2 hills showing especially excellent growth, yield and disease resistance were selected and designated SF5-1 and SF5-2.

Example 3
Production of SF6-1 and Analysis

Five hills each were multiplicated from SF5-1 and SF5-2 by cuttage from the end of July 1995 and were grown in a vinylon greenhouse. From the beginning of November, SF3 and (SF5-1 and SF5-2) were crossed and their seeds harvested.

The seeds of SF3 ×(SF5-1 and SF5-2) were sowed and cultured as described above and 600 hills were grown. From these, the plants were harvested leaving the lower 5 pairs of leaves and the leaves were separated from the plants for solar drying. The dried leaves were analyzed by thin-layer chromatography. Seventy-nine % of 600 hills had a ratio of sweetening components as SF3 and 65% had a ratio of Stevioside:Rebaudioside A of less than 1:more than 3. The average ratio of Stevioside:Rebaudioside A of all hills was found to be 1:3.

The seeds of SF6-1 were deposited on Jan. 23, 1998 with the Faculty of Agriculture of Kinki University of 3327-204, Nakamachi, Nara-shi, Nara-ken under Accession No. KM-1. Seeds of SF6-1 have also been placed on deposit with the American Type Culture Collection (ATCC), Manassas, Va., 20110, under Deposit Accession Number PTA-444 on Aug. 2, 1999.

Example 4
Production of SF6-2 and Analysis

Five hills each were multiplicated from SF5-1 and SF5-2 by cuttage from the end of July 1995 and were grown in a vinylon greenhouse and from the beginning of November, SF3 and (SF5-1 and SF5-2) were crossed and their seeds harvested.

In 1996, the seeds of SF3 ×(SF5-1 and SF5-2) were sowed and cultivated as described above and 600 hills were grown. On the day of 13th of September, the plants were harvested leaving the lower 5 pairs of leaves and the leaves were separated from the harvested plants for solar drying. The dried leaves were analyzed by thin-layer chromatography.

Forty-nine % of 600 hills had a ratio of sweetening components as SF3 and 12% were in a ratio of Stevioside:Rebaudioside A of less than 1: more than 3. The average ratio of Stevioside:Rebaudioside of all hills was found to be 1:2.17.

The production procedures and the results of analysis in Examples 1–4 are summarized in Table 2.

The ratio in parentheses show a ratio of Stevioside:Rebaudioside A (ST:RA) and the average ratio in parentheses is an average ratio of ST:RA in all plants in the same generation.

TABLE 2

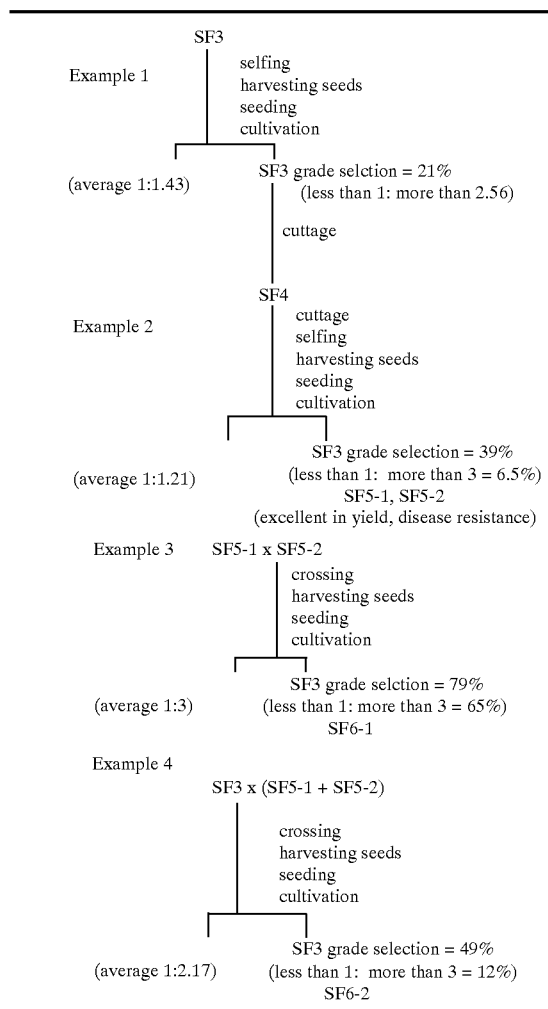

Example 5
The Sweetening Component Ratio of SF6-I, -II or -III

The dried leaves of 115 hills obtained from the seeds SF6-I which were formed on the plant SF5-1 by crossing SF5-1×SF5-2, the dried leaves of 131 hills obtained from the seeds SF6-II which were formed on the plant SF5-2 by crossing SF5-1×SF5-2, and the dried leaves of 99 hills obtained from the seeds SF6-III which were formed on the plant SF3 by crossing SF3×(SF5-1×SF5-2) were ground to prepare 50 g samples, respectively, which were analyzed for sweetening components by HPLC.

The results are shown in Table 3.

TABLE 3

|  | ST | RA | RC | ST:RA |
| --- | --- | --- | --- | --- |
| SF6-I | 3.6% | 12.7% | 1.6% | 1:3.53 |
| SF6-II | 4.1% | 10.5% | 1.5% | 1:2.56 |
| SF6-III | 3.6% | 7.8% | 1.4% | 1:2.16 |

Results

The results obtained show that SF5 has a gene expressing a high content of Rebaudioside A and can dominantly transmit the gene expressing a high content of Rebaudioside A even though SF5 has been crossed with SF3 having a gene which can not express a high content of Rebaudioside A.

The average ratio of ST:RA in the generation of the whole SF6 obtained from crossing SF5-1×SF5-2 is 1:3. In other words, it shows that a sweetening in a ratio of ST:RA of 1:more than 2.54 can be produced from plants of *Stevia rebaudiana* Bertoni by seed propagation only.

In future generations after SF6, the variety of Stevia Rebaudiana Bertoni of the present invention can show a ratio of ST:RA of 1:more than 2.54 and thus the seeds obtained by selfing can transmit the gene expressing a ratio of ST:RA of 1:more than 2.54.

Example 6
Preparation of Sweetening

Forty grams of dry leaves containing 2.56 times or more Rebaudioside A than Stevioside are extracted with 10 to 20 parts of water several times. The resulting extracts are combined and passed slowly through a column filled with 40 ml of cation-exchange resin (Amberlite IR-120B) and then a column filled with 40 ml of anion-exchange resin (Dulite AD-4). Then the treated solution is passed through a column packed with 200 ml of a resin for absorption (Amberlite XAD-2) to absorb the sweetening components, and then washed fully with water. After this water is drained from the column, which is eluted with 600 ml of methanol to isolate the sweetening components. The eluent is concentrated and further dried under a reduced pressure to obtain 5.0 g of a pale yellow powder. Yield, 12.5%.

Example 7
Sweetening Composition

Five grams of-the powder obtained in Example 6 and 5 g of dextrin were mixed to give a sweetening of the invention.

Since the number of cuttings obtained from a parent plant are limited and many parent plants are needed, it is difficult to culture a large quantity of rooted cuttings. Because of the troublesome preparation of rooted cuttings, mass production of cuttings in a short time and raising of cuttings are very difficult. According to the seed propagation of the new variety of the present invention, these disadvantages can be overcome and the present invention make it possible to remarkably reduce the constant and work involved in cultivation.

What is claimed is:

1. A SF-6 seed having ATCC Accession No. PTA-444 for cultivation of a variety of *Stevia rebaudiana* Bertoni which grows leaves comprising 2.56 times or more Rebaudioside A than Stevioside and is capable of being cultivated by seed propagation.

2. A plant produced by the seed according to claim 1.

3. A variety of *Stevia rebaudiana* Bertoni which grows leaves comprising 2.56 times or more Rebaudioside A than Stevioside and is capable of being cultivated by seed propagation which is produced from SF-6 seed having ATCC Accession No. PTA-444 or progeny thereof.

4. Progeny of a *Stevia rebaudiana* Bertoni plant grown from a SF-6 seed having ATCC Accession No. PTA-444, which grows leaves containing 2.56 times or more Rebaudioside A than Stevioside.

* * * * *